(12) United States Patent
Tripp et al.

(10) Patent No.: US 6,610,125 B2
(45) Date of Patent: Aug. 26, 2003

(54) SELECTIVE FILTRATION AND CONCENTRATION OF TOXIC NERVE AGENTS

(75) Inventors: **Car

SELECTIVE FILTRATION AND CONCENTRATION OF TOXIC NERVE AGENTS

TECHNICAL FIELD AND INDUSTRIAL APPLICABILITY OF THE INVENTION

The present invention is related generally to methods of concentrating components in gas streams containing a mixture of components, and more particularly to a method of selectively filtering and concentrating target molecules such as toxic nerve agents in a gas stream mixture.

BACKGROUND OF THE INVENTION

Semiconducting metal oxide (SMO) based sensors for chemical warfare agent detection have extreme sensitivity (parts per billion) and versatility. However, SMO based sensors exhibit poor selectivity and this is a major barrier to the implementation of this technology. In many cases, the sensor response to a target molecule is indistinguishable from the myriad of other molecules present in the gas stream. This problem of detection selectivity would clearly benefit from the development of materials and methods that can be used to selectively filter, separate, and concentrate specific target molecules from gas stream mixtures before reaching the SMO sensor.

Various methods are known for concentrating specific molecules in a gaseous mixture. For example, U.S. Pat. No. 6,171,378 to Manginell et al. discloses a chemical preconcentrator used to accumulate and concentrate one or more chemical species of interest in a gaseous mixture, and then rapidly release the concentrated chemical species upon demand for chemical analysis. The preconcentrator includes a substrate having a suspended membrane, a resistive heating element disposed on a surface of the membrane, and a sorptive material disposed on a surface of the membrane. The chemical species of interest is adsorbed on the sorptive material, and then the heating element is activated to create a thermal pulse that releases the chemical species from the sorptive material.

Unfortunately, the use of a thermal pulse to dislodge a target molecule from an adsorbent cannot achieve a high degree of selectivity between the target molecule and other similar molecules. For instance, a thermal pulse cannot effectively separate different organophosphonate compounds from each other or from other adsorbed interferent molecules. The organophosphonates include sarin and other toxic nerve agents, but the majority of organophosphonates and other adsorbed interferent molecules are harmless molecules. Consequently, a thermal pulse would not be useful for selectively filtering and concentrating the toxic nerve agents from other adsorbed interferent molecules in a gas stream mixture. Therefore, it would be desirable to provide an effective method of selectively filtering and concentrating target molecules such as toxic nerve agents.

SUMMARY OF THE INVENTION

The above object as well as others not specifically enumerated are achieved by two separate methods according to the invention for separating a target molecule from a non-target molecule in a gas stream. Preferably, the target molecule is an organophosphonate such as a nerve agent. In a particular embodiment, the method increases the relative concentration of the target molecule in the gas stream so that it can be more easily detected by a semiconducting metal oxide based sensor. In a first step of the first method, a gas stream is passed through an adsorbent. The gas stream contains molecules of the target molecule in a mixture containing molecules of at least one non-target molecule. Preferably, the adsorbent is a metal oxide such as a silica. Both the target and non-target molecules are adsorbed on the adsorbent. In a second step, another gas stream containing molecules of a chemical displacer is passed through the adsorbent. The molecules of the chemical displacer adsorb on the adsorbent to selectively displace the target molecules from the adsorbent while leaving the non-target molecules adsorbed. The chemical displacement causes the displaced target molecules to enter the gas stream. The gas stream can then be passed through a semiconducting metal oxide based sensor to detect the target molecules. Alternatively, the adsorbed chemical displacer displaces the non-target molecules while leaving the target molecules adsorbed on the adsorbent surface. In either case, a separation of the target and non-target molecules is achieved.

In the second method, an adsorbent is pretreated with a chemical displacer so that chemical displacer molecules are adsorbed on the adsorbent. A gas stream is passed through the adsorbent, the gas stream containing target molecules mixed non-target molecules. The target molecules adsorb on the adsorbent while the non-target molecules do not adsorb and instead remain in the gas stream. The chemical displacer molecules are selectively adsorbed relative to the non-target molecules to prevent their adsorption on the adsorbent. Alternatively, the chemical displacer can be selectively adsorbed relative to the target molecules, so that the non-target molecules adsorb on the adsorbent while the target molecules do not adsorb and remain in the gas stream.

Various objects and advantages of this invention will become apparent to those skilled in the art from the following detailed description of the preferred embodiments, when read in light of the accompanying drawings.

BRIEF DESCRIPTION OF THE DRAWINGS

FIG. 1 shows infrared spectra of silica exposed to different target molecules.

FIG. 2 shows infrared spectra of silica exposed to different chemical displacers.

FIG. 3 is a diagram illustrating the selective displacement of a target molecule by a chemical displacer from the surface of silica.

FIG. 4 is a diagram illustrating the selective displacement of two other target molecules by another chemical displacer from the surface of silica.

FIG. 5 is a diagram illustrating the selective displacement of another target molecule and a portion of a non-target molecule by another chemical displacer from the surface of silica.

FIG. 6 is a diagram illustrating the selective displacement of another target molecule by another chemical displacer from the surface of silica.

FIG. 7 is a diagram of a first filtering strategy for separating different target molecules in a gas stream from each other by the use of different chemical displacers.

FIG. 8 is a diagram of a second filtering strategy for separating different target molecules in a gas stream from each other by the use of different chemical displacers.

DETAILED DESCRIPTION AND PREFERRED EMBODIMENTS OF THE INVENTION

The present invention provides an effective method of increasing the relative concentration of a target molecule in a gas stream mixture. In the method, a first gas stream is passed through an adsorbent. The first gas stream contains molecules of the target molecule in admixture with molecules of at least one non-target molecule. Passing the gas stream through the adsorbent causes the molecules of the target molecule and the molecules of the non-target molecule to adsorb on the adsorbent.

The adsorbent can be any material which is effective to adsorb the target and non-target molecules from the gas stream mixture. For instance, in some embodiments of the method of the invention, suitable adsorbents may include materials such as metal oxides, polymers/plastics, pigments, calcium carbonate, or kaolin. Preferably, the adsorbent is a metal oxide such as silica, alumina, titania, aluminum oxide, magnesium oxide, or a zeolite. More preferably, the adsorbent is selected from silicas such as fumed silicas, silica gels, precipitated silicas, and meso-porous silicas.

The target molecule can be any molecule of interest contained in a gas stream mixture. Of particular interest are organophosphonates such as nerve agents and pesticides. Some examples of organophosphonate nerve agents are sarin, soman, and tabum. These molecules have the same basic molecular structure with different groups on the end. Some examples of organophosphonate pesticides are malathion and phosmet. Several other organophosphonate molecules are of particular interest because they are model compounds for toxic nerve agents such as sarin. Such organophosphonates include, for example, dimethyl methyl phosphonate (DMMP), trimethyl phosphate (TMP), methyl dichlorophosphate (MDCP), and trichlorophosphate (TCP). The adsorption of these molecules on metal oxides such as silica is of particular interest.

In this regard, we have found that the adsorption on silica of organophosphonate compounds differing in the number of methoxy groups (0, 1, 2, or 3) attached to the central P atom occurs through multiple H-bonds to the surface SiOH groups with the P=O and/or methoxy functionalities. The strength of the H-bond with the surface SiOH groups of the silica was determined by the shift in the SiO-H stretching mode located at 3747 cm$^{-1}$ in the infrared spectrum, and these values are listed in bold in Table 1:

TABLE 1

Shift in frequency of the SiOH stretching mode at 3747 cm$^{-1}$ after the adsorption of the following compounds.

| Compound | $v_{OH}$ | Ref |
|---|---|---|
| n-C$_6$H$_{14}$ | 3701 | 19 |
| Cyclohexane | 3699 | 19 |
| CCl$_4$ | 3690 | 19 |
| Benzene | 3688 | 19 |
| CH$_3$NO$_2$ | 3683 | 19 |
| CH$_3$CN | 3670 | 19 |
| H$_2$CO | 3493 | 24 |
| TCP | 3488 | 18 |
| CH$_3$OH | 3470 | 18 |
| CH$_3$CHO | 3447 | 24 |
| MDCP | 3425 | 18 |
| CH$_3$COC$_2$H$_5$ | 3411 | 24 |
| Acetone | 3402 | 24 |
| Cyclopentanone | 3372 | 24 |
| Cyclohexanone | 3348 | 24 |
| 1,4-dioxane | 3327 | 19 |
| t-Butanol | 3325 | 27 |
| 2-cyclohexene-1-one | 3324 | 24 |
| TMP | 3262 | 18 |
| (C$_2$H$_5$)$_2$O | 3230 | 19 |
| DMMP | 3223 | 18 |
| Tetrahydrofuran | 3205 | 19 |

TABLE 1-continued

Shift in frequency of the SiOH stretching mode at 3747 cm$^{-1}$ after the adsorption of the following compounds.

| Compound | $v_{OH}$ | Ref |
|---|---|---|
| Pyridine | 2830 | 19 |
| Triethylamine | 2667 | 18 |

The greater the shift of the 3747 cm$^{-1}$ band to lower frequency, the stronger the H-bond. Cl$_3$P=O (TCP) adsorbs through a single H-bond with the P=O group shifting the SiOH band to 3488 cm$^{-1}$ and is easily removed by evacuation at room temperature. However, Cl$_2$(OCH$_3$)P=O (MDCP) showed a slightly stronger H-bond than TCP (shift to 3425 cm$^{-1}$) and was only removed after evacuation at 150° C. This difference occurs because MDCP absorbs through two H-bonds per molecule with the P=O and methoxy groups.

Thus, the adsorbed strength depends on both the strength of the individual H-bonds to the surface and the number of these bonds per molecule. The importance in the number of bonds per molecule is evident when comparing the adsorption strength of DMMP and TMP. DMMP adsorbed through two strongly H-bonded methoxy groups shifting the SiOH band to 3223 cm$^{-1}$ and was eliminated at 300° C. On the other hand, (OCH$_3$)$_3$P=O (TMP) was eliminated at a higher temperature (400° C.) than DMMP despite having a slightly weaker H-bond (shift to 3262 cm$^{-1}$). This is because TMP adsorbs through three methoxy groups while DMMP adsorbs through two methoxy groups per molecule.

While each class of organophosphonates (i.e., 0, 1, 2 or 3 methoxy groups) completely desorbed with evacuation at different temperatures, the desorption of each compound proceeds over a broad temperature range. Thus, in terms of a selective filter, the use of a temperature pulse would be of limited use for selectively expelling a particular class of organophosphonate compounds from the surface. For example, while MDCP is completely desorbed at 150° C., at this same temperature approximately 70% and 50% of the total DMMP and TMP is also desorbed from the surface.

The method of the invention achieves a higher selectivity in desorption than is possible with a thermal pulse by using a chemical displacer to exchange positions with a specific H-bonded molecule on the silica surface. We determined that the use of particular amines and other molecules as chemical displacers provides a method to selectively cleave organophosphonates from silica surfaces. Such amines are useful because they adsorb on the silica through multiple H-bonds with the surface SiOH groups. We investigated the use of chemical displacers as described below, by studying the competitive adsorption/desorption of the amine based displacers and organophosphonate molecules (TCP, MDCP, DMMP, TMP) on silica. Specifically, we employed infrared spectroscopy to follow the relative amounts of each adsorbed molecule on the silica surface.

Experimental

The fumed silica Aerosil A380 with a surface area of 380 m$^2$g$^{-1}$ was obtained from DeGussa AG. Preparation of the silica consisted of evacuation at 400° C. for 30 minutes followed by cooling to room temperature. This pretreatment removes the H-bonded SiOH groups, leaving isolated SiOH groups represented by a sharp infrared band at 3747 cm$^{-1}$. It is the isolated SiOH groups that form H-bonds with the various compounds used in this study. Difference spectra are plotted where the reference spectrum is recorded through the thin film silica.

The following set of experiments was used to evaluate competitive adsorption of compound X versus compound Y. All additions of gases and recording of spectra were done at room temperature. Three separate experiments were performed for each pair-wise comparison. In experiment 1, compound X was introduced to the bare silica by adding an excess quantity of vapor for 5 minutes followed by evacuation for 15 minutes. An infrared spectrum of compound X adsorbed on silica was then recorded. This was followed by the recording of a second infrared spectrum after an excess quantity of vapor of compound Y was added for a short duration (20–30 seconds) to the X treated silica, followed by evacuation for 5 minutes. From a comparison of the two spectra, it was possible to determine which compound remained adsorbed on the surface. If there was no evidence of displacement of compound X (i.e., no change in the infrared spectra), compound Y was again added for an additional 5 minutes followed by evacuation for 5 minutes. In all cases, the spectrum obtained after the 5 minutes additional exposure to compound Y was no different from the spectrum obtained with 20–30 seconds of exposure. The procedure for experiment 2 was the same as experiment 1 except that the order of addition was reversed (i.e., compound Y first, followed by compound X). In a third separate experiment, a 1:1 mol/mol gas mixture was added to the bare silica. In this case the mixture was added for 20–30 seconds followed by evacuation for 5 minutes.

Semiempirical energy calculations were carried out using the Austin Model 1 (AM1) method using Gausian 94 software.

DMMP, TMP, TCP, MDCP, and the various chemical displacers, TEA, 2-PyAN, EDA, and 2-methoxy-ethylamine (MEA) were purchased from Aldrich Chemical Company, Milwaukee, Wis. All reagents were used as received and were transferred to evacuable glass bulbs using standard freeze-thaw cycles. Chart 1 illustrates the structural formula of each compound.

Chart 1

Results and Discussion

Competitive adsorption of organophosphonates. In our first set of experiments we examined the competitive adsorption of the four organophosphonate compounds on silica. The spectra of adsorbed TCP, MDCP, DMMP and TMP on silica are shown in FIGS. 1a–d, respectively. Each compound produces unique bands that can be used to monitor their relative abundance on the surface. The specific integrated band that we used to monitor the amount of each adsorbed compound is listed in Table 2:

TABLE 2

The specific integrated bands used to monitor the adsorption/desorption of the indicated compounds.

| Adsorbed molecules | cm$^{-1}$ |
|---|---|
| TCP | 604 |
| MDCP | 1288 |
| DMMP | 1314 |
| TMP | 1268 |
| TEA | 1388 |
| MEA | 1460 |
| 2-PyAN | 1440 |
| EDA | 1594 |

Pair-wise comparisons with TCP are not performed because TCP forms a weak H-bond with the P=O group and is completely eliminated from silica with evacuation at room temperature. In contrast, MDCP, DMMP and TMP adsorb on silica at room temperature and thus, from a filtering standpoint, separation of TCP from the other three compounds could be accomplished by passing the gas stream through silica. The TCP would pass directly through the silica filter while the other three compounds would remain adsorbed on the silica.

Figure 1:
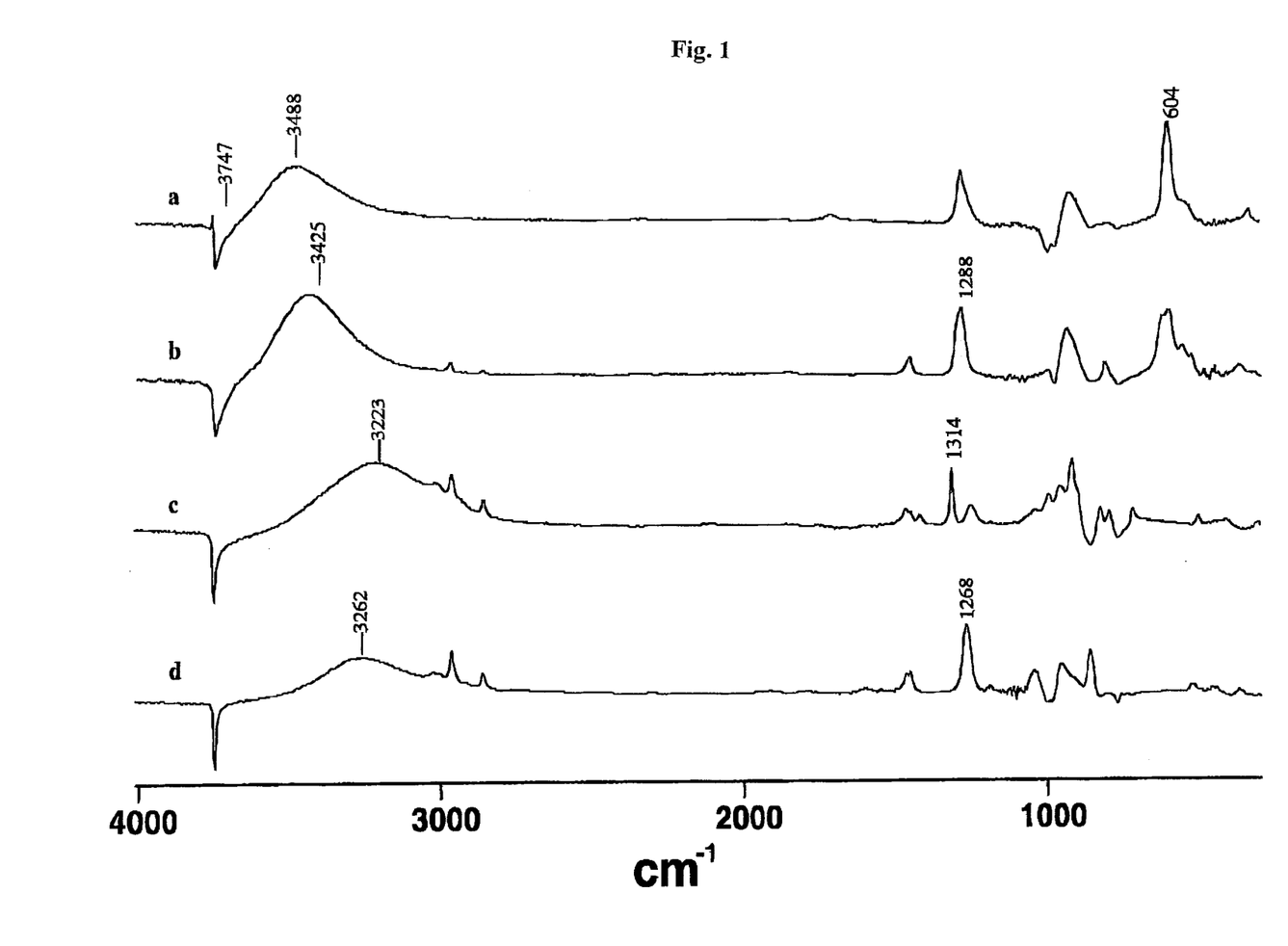

When a silica sample pretreated with MDCP is exposed to DMMP vapor, the spectrum obtained mirrors that of FIG. 1c (i.e., only adsorbed DMMP is detected). All evidence of adsorbed MDCP is removed with a single 20-second exposure to excess DMMP. In the reverse experiment, pre-adsorbed DMMP is not removed by exposure to excess MDCP. Furthermore, when a 1:1 MDCP/DMMP mixture is exposed to a bare silica sample, again, spectral features only due to adsorbed DMMP are detected. This high degree of selective adsorption between DMMP and MDCP is mirrored when the same sets of experiments are performed for DMMP verses TMP. In this case, TMP is selectively adsorbed over DMMP. Collectively, the high degree of selectivity derived from the competitive adsorption involving MDCP, DMMP and TMP demonstrates the potential selectivity when using chemical displacers. This degree of selectivity is not obtained using thermal desorption based methods.

In our pair-wise comparisons, the silica was exposed to excess quantities of each organophosphonate. In this case, there is competitive displacement because there are no free surface sites available. In sensor related applications the amount of silica needed to accomplish the filtering process would be small because the anticipated concentration of toxic organophosphonates is in the low ppm or ppb levels. Given the high surface area of the silica (380 m$^2$/g) and assuming a conservative estimate of 1.0 isolated SiOH groups/nm, it would require a liter of DMMP at a concentration of about 7000 ppm to saturate a 1 g quantity of silica. Thus, at the ppb or low ppm level there would be a sufficient number of free surface sites available to accommodate all three compounds and a competitive displacement of one organophosphonate compound by another would not occur. Therefore, a separate chemical displacer would be required for selectively removing each adsorbed organophosphonate and based on the relative adsorption strength of the organophosphonates on silica, it is possible to construct a generalized scheme for the selection of appropriate adsorption strength required for each chemical displacer (labeled A, B, and C):

Identification of Chemical Displacers A–C. A displacer molecule is not needed between TCP and MDCP because an organophosphonate such as TCP that is adsorbed solely through a single H-bond with the P=O group, is easily removed from silica by simple evacuation or by a gas stream purge. To help identify potential displacers A, B and C, we recall that the adsorption strength of each organophosphonate depends on 1) the strength of the H-bond with the surface SiOH group, and 2) the number of such bonds per molecule. The strength of the H-bond can be determined from the shift in the SiOH band and these are listed for various functional groups in Table 1.

Figure 2:
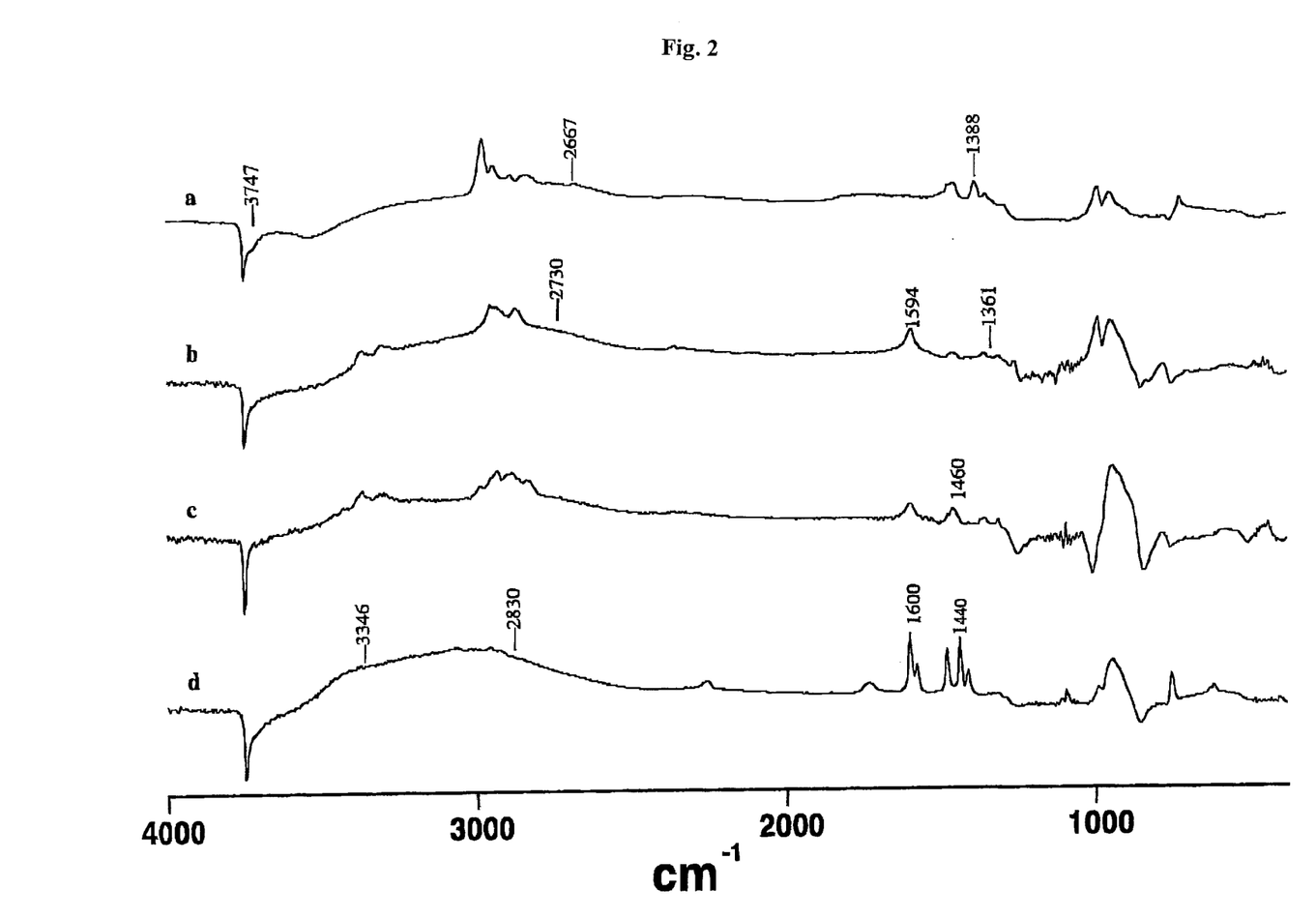

Our first measurements of competitive adsorption tested triethylamine (TEA) as a displacer against MDCP, as well as TEA vs. DMMP and TEA vs. TMP. TEA forms the strongest single H-bond with the surface SiOH groups (see Table 1). The spectrum of adsorbed TEA on silica is shown in FIG. 2a. A strong H-bond is evidenced by the shift in the band at 3747 cm$^{-1}$ to about 2667 cm$^{-1}$. To the best of our knowledge, this is the largest frequency shift observed for a H-bonded molecule on silica. In our pair-wise comparison experiments, it is found that TEA completely removes MDCP and does not displace either adsorbed DMMP or TMP.

Figure 3:
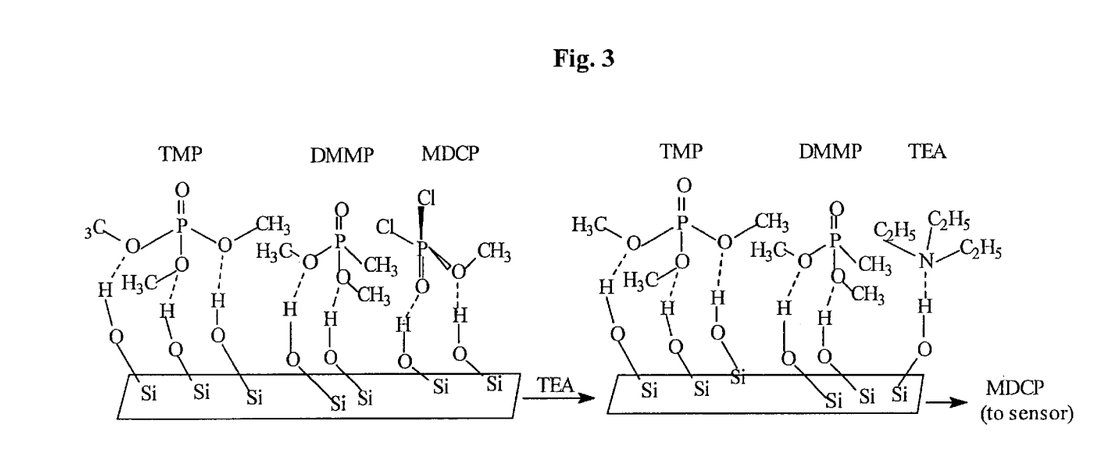

As shown in FIG. 3, the inability of TEA to displace DMMP or TMP confirms that these two organophosphonates adsorb by multiple H-bonds between the methoxy groups and the surface SiOH groups. TEA forms a stronger H-bond than the individual H-bonds for either adsorbed DMMP or TMP. While TEA shifts the SiOH stretching mode to about 2667 cm$^{-1}$, this band shifts only to 3262 cm$^{-1}$ and 3223 cm$^{-1}$ for adsorbed TMP and DMMP, respectively. The reason TEA does not displace either TMP or DMMP is that both organophosphonates form multiple H-bonds between the methoxy groups and the surface SiOH groups. On the other hand, MDCP is bonded through a single H-bond with the methoxy group and a much weaker H-bond with the P=O and therefore is easily displaced by the more strongly H-bonded TEA. As a result, TEA satisfies the criteria outlined for displacer A in the above scheme.

Since TEA forms the strongest known H-bond with the isolated SiOH groups, displacer B or C will require a molecule that forms multiple H-bonds to the surface. Possible structures for displacer B or C are of general form X—Y where X and Y refer to the functionalities included in the compounds listed in Table 1. To selectively displace DMMP and not TMP from silica, the displacer B molecule will have to form a stronger bond than DMMP (H-bonded through two methoxy groups per molecule), but one that is weaker than TMP (H-bonded through three methoxy groups per molecule).

Based on the results obtained with adsorbed TEA, we expect that a diamine such as ethylenediamine (EDA) would difunctionally adsorb and thus displace the adsorbed DMMP from the surface. Each individual amine H-bond for adsorbed EDA would be stronger than the corresponding individual methoxy H-bond for adsorbed DMMP. FIG. 2b is the infrared spectrum of adsorbed EDA on silica. The combination of a single band at 1594 cm$^{-1}$ due to the H-bonded NH2 bending mode and the absence of a band at 1620 cm$^{-1}$ for free amine shows that each EDA molecule adsorbs through two H-bonds with both amine groups. Furthermore, the shift of the SiOH stretching mode to about 2730 cm$^{-1}$ shows that each individual H-bond is stronger than the corresponding H-bonded methoxy groups of either adsorbed DMMP or TMP.

Figure 4:
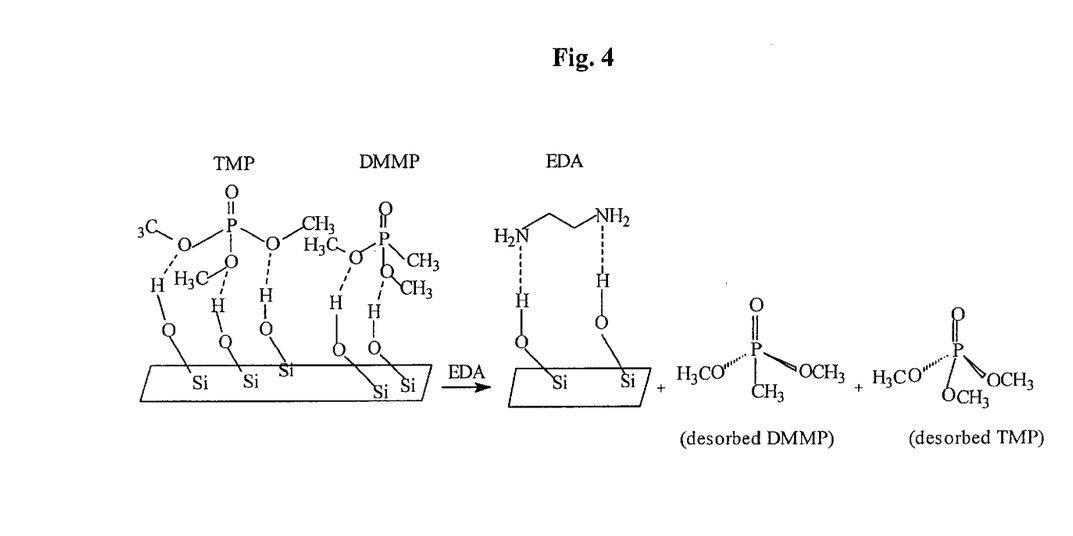

While the infrared spectra obtained for the experiments of EDA vs. DMMP show that DMMP is displaced from the surface by EDA, the same result is obtained for EDA vs. TMP. As depicted in FIG. 4, adsorbed EDA is of sufficient strength to remove both DMMP and TMP. This result shows that two surface H-bonds through the amine moieties of EDA are much stronger than the three surface H-bonds of the TMP methoxy groups on silica. Nevertheless, these results do show that EDA does satisfy the conditions required by the displacer C.

For a clue to the possible candidate molecules for displacer B we again refer to the relative H-bond strengths listed in Table 1. At a minimum, we need a bifunctional displacer because the strongest singly H-bonded amine (TEA) does not remove DMMP. At the upper limit, we know that a displacer anchored through two H-bonded amine functionalities (EDA) is too strongly bonded to the surface because it displaces TMP. Given these boundary conditions on the lower and upper limits, likely candidate displacers are hetero-bifunctional molecules where one functionality is an amine and the second is a weaker H-bonded functionality selected from the list in Table 1.

The first molecule tested was methoxy ethylamine (MEA) because it satisfies our criteria by having one amine and one methoxy group separated by an ethylene group (see Chart 1). The infrared spectrum of MEA adsorbed on silica (FIG. 2c) shows that each MEA molecule adsorbs through H-bonds with both the methoxy and amine groups with the surface SiOH groups. The absence of a strong methoxy mode of the gaseous molecule at 1138 cm$^{-1}$ (not shown), the negative band at 3747 cm$^{-1}$ and the appearance of a broad feature near 3300 cm$^{-1}$ is clear evidence that a H-bond exists between the methoxy group and the surface SiOH groups. The shift of the free amine mode at 1626 cm$^{-1}$ in the gas phase to 1594 cm$^{-1}$ along with a broad band near 2650 cm$^{-1}$ is evidence of a H-bond between the amine functionality and the surface SiOH groups.

Figure 5:
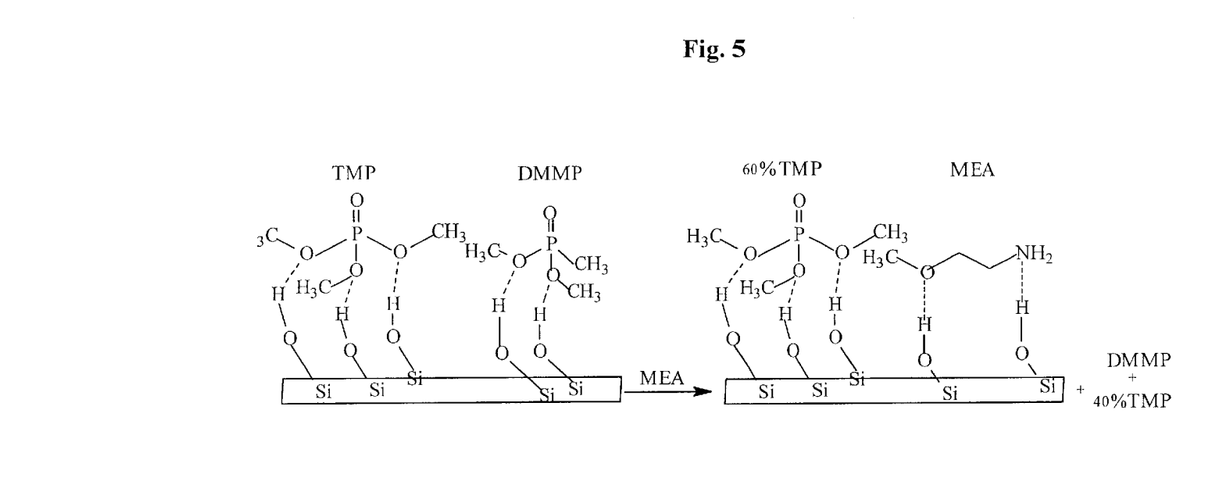

The competitive adsorption experiments of DMMP vs. MEA show that MEA completely displaces DMMP from the silica surface and thus, MEA satisfies the lower limit criterion for displacer B molecule. In essence, the combination of one H-bonded amine and one H-bonded methoxy group in the MEA are stronger than the two H-bonds formed with the methoxy groups of a DMMP molecule (see FIG. 5). However, when a silica sample containing adsorbed TMP (adsorbed on silica through three methoxy groups) is exposed to excess MEA for 5 minutes followed by evacuation for 2 minutes at room temperature, the spectrum obtained shows spectral bands due to a mixture of adsorbed TMP and MEA on the surface. Comparison of the integrated peak area of the TMP band at 1268 cm$^{-1}$ reveals that MEA displaces about 40% of the adsorbed TMP. While MEA is an improvement over EDA, it is still too strongly adsorbed to satisfy the upper limit conditions for displacer B.

The result obtained with adsorbed MEA shows that the displacer B will require a molecule that is slightly weaker than MEA in its H-bonding interaction with silica. From the list in Table 1, 2-pyridylacetonitrile (2-PyAN) is a good candidate because when compared to MEA, a H-bond with pyridine is slightly weaker than a secondary amine and a H-bond formed with a cyano group is slightly weaker than one formed with a methoxy group.

Figure 6:
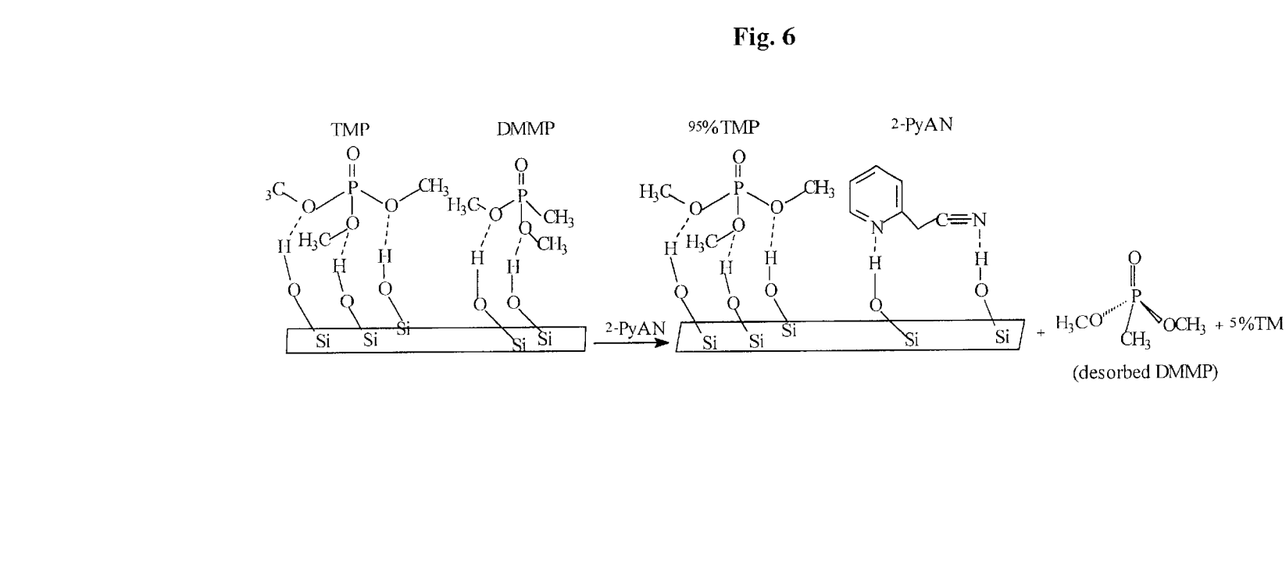

The infrared spectrum of the adsorbed 2-PyAN is shown in FIG. 2d. The negative band at 3747 cm$^{-1}$ and the appearance of two broad features at 3346 cm$^{-1}$ and 2830 cm$^{-1}$ indicate the formation of H-bonds through the nitrile and pyridyl moieties, respectively. These shifts are slightly less than the shifts obtained with the secondary amine (near 2650 cm$^{-1}$) and methoxy (3300 cm$^{-1}$) groups of adsorbed MEA. In the competitive experiments involving DMMP vs. 2-PyAN we find that the 2-PyAN displaces all of the adsorbed DMMP. In the TMP vs. 2-PyAN experiments, exposure of a TMP treated silica to 2-PyAN shows that about 95% of the adsorbed TMP remains on the surface. Thus, 2-PyAN is a good candidate molecule for displacer B (see FIG. 6).

Filtering strategies. Based on the identification of suitable molecules for displacers A–C, it is now possible to construct theoretical schemes for the selective chemical displacement of the four classes of organophosphonates from silica. One approach (FIG. 7) operates by proceeding up the scale of increasing adsorption strengths and a second approach (FIG. 8) starts from the top of the adsorption strength and works downward.

Figure 7:
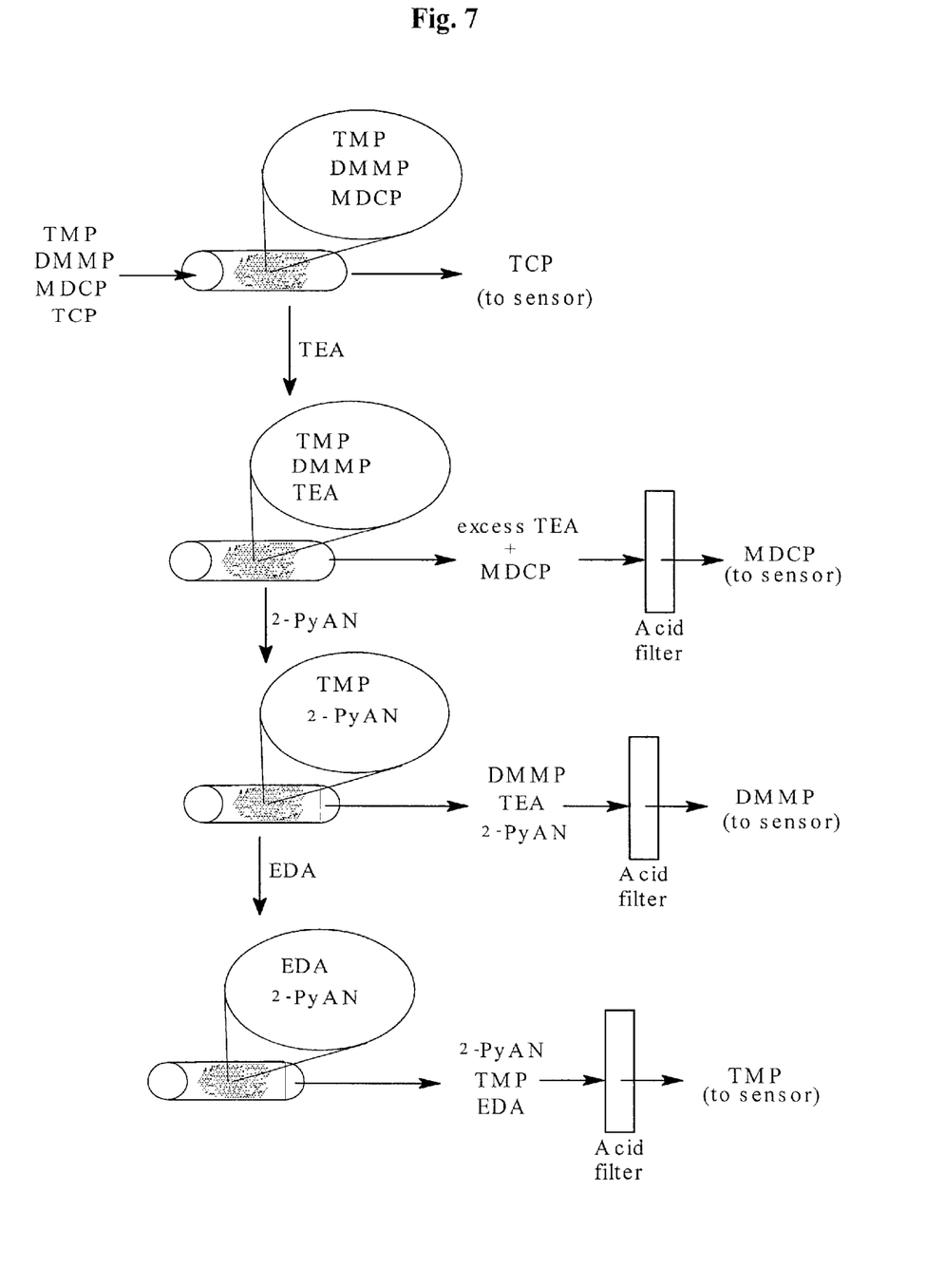

One strategy would involve sequential addition of the chemical displacers (see FIG. 7). In the first step TMP, DMMP and MDCP would be concentrated on silica and separated from TCP by passing the gas stream through a silica filter. A TEA pulse would then pass through the silica and the effluent gas stream would contain the displaced MDCP and excess TEA. Subsequent removal of the TEA from the MDCP/TEA mixture could be accomplished by passing the mixture through an acid filter converting the TEA to a nonvolatile salt. In a similar manner sequential pulses of 2-PyAN would be used to displace DMMP and TEA followed by an EDA pulse to finally remove TMP. In this strategy, the amine chemical displacers would be added to the gas stream and would have to be separated by inserting an additional filter to remove the amines.

Figure 8:
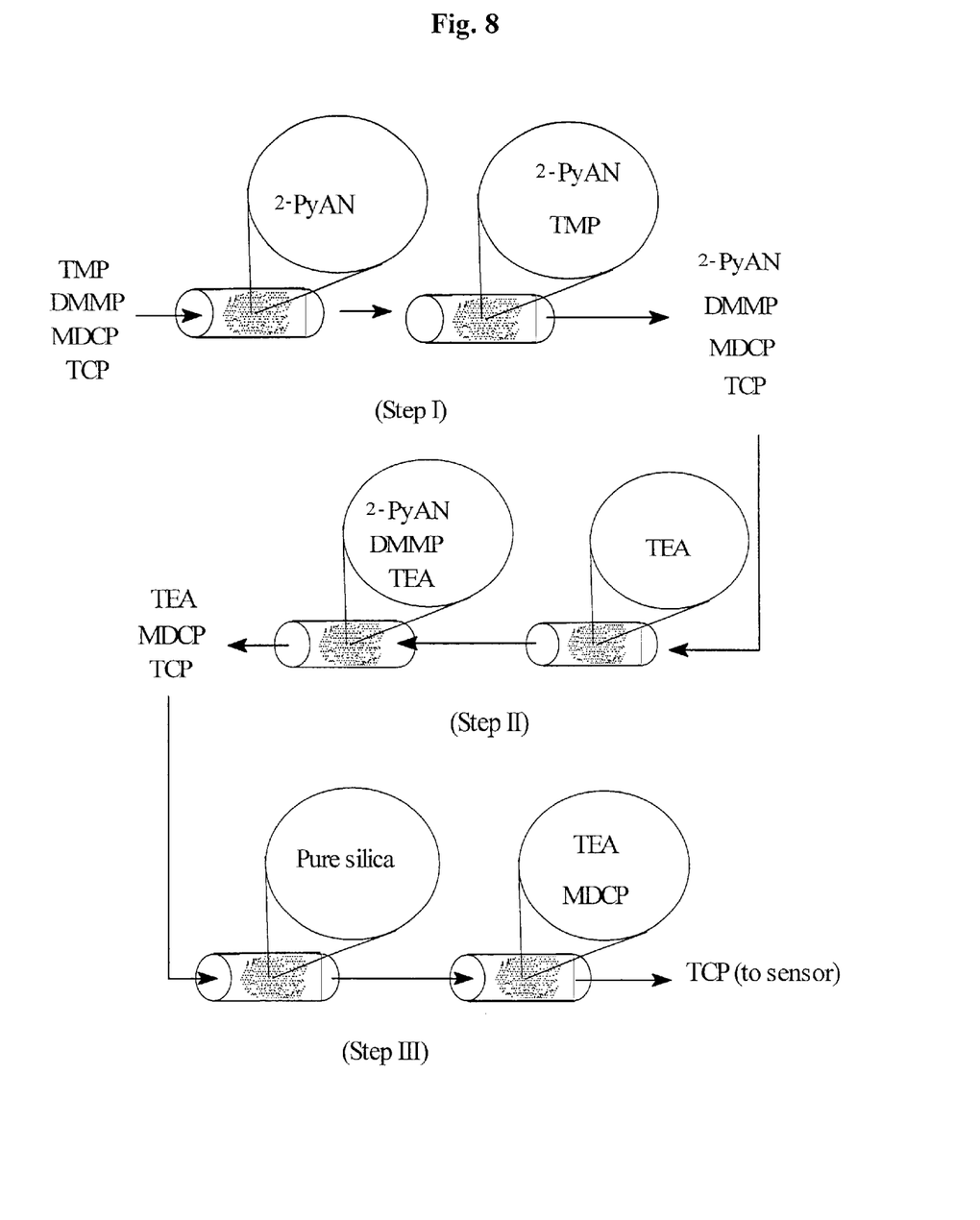

An alternative filtering strategy could be used to avoid generating amines in the gas stream. This is depicted in FIG. 8. In the first filter the gas stream would encounter silica pretreated with 2-PyAN. TMP would selectively adsorb liberating a small amount of 2-PyAN in the process. The gas stream would then pass through a silica filter doped with TEA. DMMP and 2-PyAN would adsorb liberating some TEA. Finally, the gas stream would pass through silica where MDCP and TEA would adsorb. TCP would pass through the silica and be detected separately. In this configuration, each filter now contains one organophosphonate and an adsorbed amine. HCl vapor could then be added to convert the amines to salts and the organophosphonates would then be released by applying a thermal pulse.

Extension to Sarin. Our purpose in studying the adsorption of DMMP and the other organophosphonates is that they are simulants for toxic nerve agents. While we are not equipped or have the desire to perform experiments with live agents, the schemes described here demand some estimate of the relative adsorption strength of the live agents on silica. For example, sarin, $O=PF(CH_3)(OCH(CH_3)_2)$, contains one methoxy group and thus we expect it to be more weakly adsorbed than DMMP. An estimate on the strength of the H-bond between the methoxy group of sarin and the surface SiOH groups can be deduced from AMI semi-empirical calculations. Table 3 lists the partial charge on the methoxy oxygen atoms based on Mulliken population analysis:

TABLE 3

Partial charges on the methoxy oxygen atoms based on Mulliken population analysis.

| Compound | Charges of the methoxy oxygen atoms |
|---|---|
| MDCP | −0.635 |
| DMMP | −0.734, −0.775 |
| TMP | −0.707, −0.745, −0.745 |
| Sarin | −0.775 |

There is good correlation with the magnitude of the charge on the oxygen atom and the shift in the SiOH band of silica for MDCP, DMMP and TMP. For example, the calculated values correctly position the H-bond strength of DMMP higher than the H-bond strength of TMP. Based on these calculations, we would expect that the adsorption strength of sarin would lie between MDCP and DMMP. The adsorbed strength would be slightly stronger than MDCP and on the same order as the individual H-bond for DMMP. Thus, we expect sarin to adsorb onto silica shifting the SiOH band to near 3223 cm$^{-1}$ and that it would be displaced by an excess TEA pulse.

The principle and mode of operation of this invention have been described in its preferred embodiments. However, it should be noted that this invention may be practiced otherwise than as specifically illustrated and described without departing from its scope.

What is claimed is:

1. A method of increasing the relative concentration of an organophosphonate in a gas stream comprising the steps of:
    passing a first gas stream through an adsorbent, the first gas stream containing molecules of the organophosphonate mixed with molecules of at least one non-target molecule, to adsorb the molecules of the organophosphonate and the molecules of the non-target molecule on the adsorbent; and then
    passing a second gas stream containing molecules of a chemical displacer through the adsorbent, so that the molecules of the chemical displacer adsorb on the adsorbent to selectively displace molecules of the organophosphonate from the adsorbent while leaving molecules of the non-target molecule adsorbed on the adsorbent, the chemical displacement causing the displaced molecules of the organophosphonate to enter the second gas stream.

2. A method according to claim 1 wherein the organophosphonate is a nerve agent.

3. A method of increasing the relative concentration of a target molecule in a gas stream so that the target molecule can be more easily detected by a semiconducting metal oxide based sensor, the method comprising the steps of:
    passing a first gas stream through an adsorbent, the first gas stream containing molecules of the target molecule mixed with molecules of at least one non-target molecule, to adsorb the molecules of the target molecule and the molecules of the non-target molecule on the adsorbent; then
    passing a second gas stream containing molecules of a chemical displacer through the adsorbent, so that the molecules of the chemical displacer adsorb on the adsorbent to selectively displace molecules of the target molecule from the adsorbent while leaving molecules of the non-target molecule adsorbed on the adsorbent, the chemical displacement causing the displaced molecules of the target molecule to enter the second gas stream; and then passing the second gas stream through a semiconducting metal oxide based sensor to detect the target molecule.

4. A method according to claim 3 wherein the chemical displacer has a high degree of selective adsorption on the adsorbent relative to the target molecule, such that the molecules of the chemical displacer chemically displace at least about 90% by weight of the molecules of the target molecule from the adsorbent.

5. A method according to claim 3 wherein the target molecule is an organophosphonate.

6. A method according to claim 5 wherein the organophosphonate is a nerve agent.

7. A method according to claim 3 wherein the adsorbent is a silica.

8. A method according to claim 3 wherein the adsorbent is a silica, and wherein the target molecule adsorbs on the silica by at least one hydrogen bond between at least one surface SiOH group of the silica and at least one functionality of the target molecule, and the chemical displacer adsorbs on the silica by at least one hydrogen bond between at least one surface SiOH group of the silica and at least one functionality of the chemical displacer, the strength of the adsorption by the target molecule and the chemical displacer being determined by the number of the hydrogen bonds and by the strength of each hydrogen bond as determined by the functionality.

9. A method of separating an organophosphonate from a non-target molecule in a gas stream comprising the steps of:
   passing a first gas stream through an adsorbent, the first gas stream containing molecules of the organophosphonate mixed with molecules of the non-target molecule, to adsorb the molecules of the organophosphonate and the molecules of the non-target molecule on the adsorbent; and then
   passing a second gas stream containing molecules of a chemical displacer through the adsorbent, so that the molecules of the chemical displacer adsorb on the adsorbent to selectively displace molecules of the non-target molecule from the adsorbent while leaving molecules of the organophosphonate adsorbed on the adsorbent.

10. A method according to claim 9 wherein the adsorbent is a silica.

11. A method of separating an organophosphonate from a non-target molecule in a gas stream comprising the steps of:
   pretreating an adsorbent with a chemical displacer so that molecules of the chemical displacer are adsorbed on the adsorbent; and
   passing a gas stream through the adsorbent, the gas stream containing molecules of the organophosphonate mixed with molecules of the non-target molecule, so that molecules of the organophosphonate adsorb on the adsorbent while molecules of the non-target molecule do not adsorb on the adsorbent and remain in the gas stream, the chemical displacer being selectively adsorbed on the adsorbent relative to the non-target molecule to prevent the adsorption of non-target molecules on the adsorbent.

12. A method according to claim 11 wherein the adsorbent is a silica.

13. A method of separating an organophosphonate from a non-target molecule in a gas stream comprising the steps of:
   pretreating an adsorbent with a chemical displacer so that molecules of the chemical displacer are adsorbed on the adsorbent; and
   passing a gas stream through the adsorbent, the gas stream containing molecules of the organophosphonate mixed with molecules of the non-target molecule, so that molecules of the non-target molecule adsorb on the adsorbent while molecules of the organophosphonate do not adsorb on the adsorbent and remain in the gas stream, the chemical displacer being selectively adsorbed on the adsorbent relative to the organophosphonate to prevent the adsorption of organophosphonate on the adsorbent.

14. A method according to claim 13 wherein the adsorbent is a silica.

15. A method of increasing the relative concentration of a target molecule in a gas stream comprising the steps of:
   passing a first gas stream through a silica adsorbent, the first gas stream containing molecules of the target molecule mixed with molecules of at least one non-target molecule, to adsorb the molecules of the target molecule and the molecules of the non-target molecule on the silica; and then
   passing a second gas stream containing molecules of a chemical displacer through the silica, so that the molecules of the chemical displacer adsorb on the silica to selectively displace molecules of the target molecule from the silica while leaving molecules of the non-target molecule adsorbed on the silica, the chemical displacement causing the displaced molecules of the target molecule to enter the second gas stream;
   wherein the target molecule adsorbs on the silica by at least one hydrogen bond between at least one surface SiOH group of the silica and at least one functionality of the target molecule, and the chemical displacer adsorbs on the silica by at least one hydrogen bond between at least one surface SiOH group of the silica and at least one functionality of the chemical displacer, the strength of the adsorption by the target molecule and the chemical displacer being determined by the number of the hydrogen bonds and by the strength of each hydrogen bond as determined by the functionality.

16. A method according to claim 15 wherein the at least one functionality of the chemical displacer is selected from the group of functionalities which are included in the following compounds: n-hexane, cyclohexane, carbon tetrachloride, benzene, methyl nitrate, methyl cyanate, formaldehyde, trichlorophosphate, methanol, acetaldehyde, methyl dichlorophosphate, methyl ethyl ketone, acetone, cyclopentanone, cyclohexanone, 1,4-dioxane, t-butanol, 2-cyclohexene-1-one, trimethyl phosphate, diethyl ketone, dimethyl methylphosphonate, tetrahydrofuran, pyridine, triethylamine, 2-pyridyl acetonitrile, methoxy ethylamine, and ethylene diamine.

17. A method according to claim 15 wherein the chemical displacer adsorbs on the silica by a plurality of the hydrogen bonds.

18. A method of separating a target molecule from a non-target molecule in a gas stream comprising the steps of:
   pretreating a silica adsorbent with a chemical displacer so that molecules of the chemical displacer are adsorbed on the silica; and
   passing a gas stream through the silica, the gas stream containing molecules of the target molecule mixed with molecules of the non-target molecule, so that molecules of the target molecule adsorb on the silica while molecules of the non-target molecule do not adsorb on the silica and remain in the gas stream, the chemical displacer being selectively adsorbed on the silica relative to the non-target molecule to prevent the adsorption of non-target molecules on the silica;

wherein the target molecule adsorbs on the silica by at least one hydrogen bond between at least one surface SiOH group of the silica and at least one functionality of the non-target molecule, and the chemical displacer adsorbs on the silica by at least one hydrogen bond between at least one surface SiOH group of the silica and at least one functionality of the chemical displacer, the strength of the adsorption by the target molecule and the chemical displacer being determined by the number of the hydrogen bonds and by the strength of each hydrogen bond as determined by the functionality.

* * * * *